United States Patent
Choudhary et al.

(10) Patent No.: US 7,094,915 B2
(45) Date of Patent: Aug. 22, 2006

(54) BIPHASIC PROCESS FOR EPOXIDATION OF OLEFINIC COMPOUND USING CHROMATE OR DICHROMATE CATALYST

(76) Inventors: Vasant Ramchandra Choudhary, National Chemical Laboratory, Pune 411 008, Maharasthra (IN); Nilesh Sudhir Patil, National Chemical Laboratory, Pune 411 008, Maharasthra (IN)

( * ) Notice: Subject to any disclaimer, the term of this patent is extended or adjusted under 35 U.S.C. 154(b) by 0 days.

(21) Appl. No.: 10/721,796

(22) Filed: Nov. 26, 2003

(65) Prior Publication Data
US 2005/0113586 A1   May 26, 2005

(51) Int. Cl.
*C07D 301/19* (2006.01)
(52) U.S. Cl. .................. 549/529; 549/525; 549/524; 549/518
(58) Field of Classification Search ............ 549/529, 549/525, 524, 518
See application file for complete search history.

(56) References Cited

U.S. PATENT DOCUMENTS

| | | | | |
|---|---|---|---|---|
| 2,793,975 A | * | 5/1957 | Mark .................... | 514/475 |
| 2,833,787 A | * | 5/1958 | Carlson et al. .......... | 549/531 |
| 3,351,635 A | * | 11/1967 | Kollar .................. | 549/529 |
| 3,523,956 A | * | 8/1970 | Richard ................ | 549/529 |
| 3,624,464 A | * | 11/1971 | Gentry ................. | 257/154 |
| 4,367,342 A | * | 1/1983 | Wulff et al. ............ | 549/529 |
| 4,864,041 A | * | 9/1989 | Hill .................... | 549/513 |
| 6,624,318 B1 | * | 9/2003 | Muller et al. ........... | 549/529 |

OTHER PUBLICATIONS

Rothenberg et al., Pyridines as Bifunctional Co-Catalyst in the CrO3-Catalyzed Oxygenation of Olefins t-Butyl Hydroperoxide, Journal of Molecular Catalysis A: Chemical 136 (1998) 253-262.*

* cited by examiner

*Primary Examiner*—Johann Richter
*Assistant Examiner*—Chukwuma Nwaonicha
(74) *Attorney, Agent, or Firm*—Nixon & Vanderhye P.C.

(57) ABSTRACT

The present invention relates to a biphasic process for the epoxidation of an organic compound by organic compound by organic hydroperoxide. More particularly, the present invention relates to a biphasic process for the epoxidation of an organic compound by organic hydroperoxide to the corresponding epoxide, using chromate or dichromate anions as the catalyst in aqueous medium.

15 Claims, No Drawings

BIPHASIC PROCESS FOR EPOXIDATION OF OLEFINIC COMPOUND USING CHROMATE OR DICHROMATE CATALYST

FIELD OF THE INVENTION

The present invention relates to a biphasic process for the epoxidation of an organic compound by organic compound by organic hydroperoxide. More particularly, the present invention relates to a biphasic process for the epoxidation of an organic compound by organic hydroperoxide to the corresponding epoxide, using chromate or dichromate anions as the catalyst in aqueous medium.

The process of the invention can be used for the production of organic epoxides, which are fine chemicals and/or used as intermediates in the preparation of fine chemicals or specialty chemicals in perfumery, dyes, pharmaceutical and other chemical industries.

BACKGROUND OF THE INVENTION

Epoxides are a general class of compounds, which contains an oxarine ring,

They are conventionally produced by epoxidation of olefinic compounds containing olefinic group, C=C. A few processes for the liquid phase epoxidation of olefinic compounds, to corresponding epoxides, using both the homogeneous and heterogeneous solid catalysts, have been described in the prior art. U.S. Pat. No. 4,864,041 (1989) discloses a process for the homogeneous epoxidation reaction of an olefinic organic substrate, using transition metal-substituted polyoxometallate catalyst, the transition metal used was Co, Mn, Cu, Fe, or Cr. U.S. Pat. No. 5,155,241 (1992) styrene oxide is prepared by reacting styrene and hydrogen peroxide in biphasic liquid system in the presence of a bis (tri-n-alkyltinoxy) molybdic acid and an inorganic anion. U.S. Pat. No. 5,223,613 (1993) discloses an olefin epoxidation process in which an olefinically unsaturated substrate is converted with an oxidizing agent in the presence of a catalytic amount of a bimetallic complex, each of the two metallic elements of which is selected from V, Cr, Mn, Fe, Co, Ni, Cu, Mo, Ru, Rh, Pd, W, Re, Os, Ir, and Pt. U.S. Pat. No. 5,510,516 (1996) discloses a process for epoxidation of unsaturated acrylates by contacting it with hydrogen peroxide or organic peracids in the presence of alkali metal molybdates or tungstates or heteropolyacid.

A few processes utilizing heterogeneous solid catalysts for the epoxidation of olefinic organic compounds have also been described in the prior art. According to U.S. Pat. No. 5,319,114 (1994), olefins are converted to epoxides by reacting them with an organic peroxide in the presence of a heterogeneous catalysts comprised of a carbon molecular sieve containing transition metal from the group IVA, VA, VIA, and VIIA transition elements, such as Ti, W, Cr, V, Mo, Ni, or Re. However, there is always a high possibility of leaching out of transition metals from the colid catalyst during the epoxidation process, causing a loss of catalytic activity and/or selectivity and also making difficult the separation of the leached out components from the reaction mixture [Reference I.W.C.E. Arends and R. A. Sheldon, Applied Catalysis A: General. Volume 212, page 175–187, 2001]

European Patent 0568336A2 discloses a process for producing an epoxide by contacting an olefin with hydrogen peroxide in the presence of a titanium silicate zeolite catalyst. U.S. Pat. No. 6,194,591 (2001) also discloses an olefin epoxidation process using a titanium zeolite catalyst modified with Pt, Pd, or Cu compound. However, since the titanium silicate zeolite catalysts are acidic in nature they also catalyze the epoxide isomerisation and/or epoxide ring opening, thereby reducing the selectivity for the formation of epoxide in the epoxidation process over these catalysts. For example, the isomerisation of styrene oxide over Ti containing zeolite catalyst is quite fast and hence phenyl acetaldehyde instead of styrene oxide is formed in the epoxidation reaction [European Patent 0,100,117A1 (1984); Z. Fu et al. Microporous and Mesoporous Materials, volume 29, page 351–359, 1999].

Conventionally, epoxides are produced by reacting organic olefinic compound with peracids. For example styrene oxide is generally prepared adopting a procedure described in Japanese Patent Laid Open No. 149271 (1990), which involves the epoxidation of styrene by an organic peracid. However, this process has drawbacks, such as i) low epoxide selectivity or yield due to decomposition of peracid resulting free radicals which are involved in the reaction with styrene, ii) organic acid by products produced from the [peracid cause styrene oxide cleavages, ultimately causing low epoxide selectivity or yield, iii) even peracetic acid which is commercially easily available among organic peracids is very expensive and iv) handling and use of organic peracid are dangerous and hence the epoxidation of olefinic compound by organic peracid is hazardous, need close attention.

This invention is, therefore, made with the following objects so that most of the drawbacks or limitations of the prior art processes for the epoxidation of olefinic organic compounds could be overcome:

OBJECTS OF THE INVENTION

The main object of this invention is to provide a liquid phase process for the epoxidation of an olefinic organic compound to corresponding epoxide with high selectivity for epoxide formation, using a novel catalyst with high activity and high selectivity.

Another object of the invention is to provide a liquid phase process for the epoxidation of an olefinic organic compound to corresponding epoxide, using a novel catalyst, which is easily separable from the reaction or products in the process.

SUMMARY OF THE INVENTION

The present invention provides a biphasic process for liquid phase epoxidation of an olefinic compound comprising at least one olefinic group to an epoxide by an organic hydroperoxide, using a catalyst comprising chromate or dichromate anions, comprising:

i) contacting a liquid mixture containing the olefinic compound and the organic hydroperoxide compound with an aqueous solution of the catalyst in a stirred batch reactor in the presence of water such that the olefinic compound and the organic hydroperoxide are present in non-aqueous organic phase and the catalyst is present in dissolved form in aqueous phase; the mole ratio of organic hydroperoxide to olefinic compound being in the range of 0.1 to 10, the weight ratio of catalyst to olefinic compound being in the range of 0.0005 to 0.5;

ii) separating the aqueous layer containing the catalyst; and iii) separating reaction products and unconverted reactants from non-aqueous organic phase.

In one embodiment of the invention step (i) above is carried out at a temperature in the range of 25° C. to 250° C. and for a contacting period in the range of 0.1 h to 100 h and at a pressure of at least 1 atm.

In another embodiment of the invention, the reaction products comprise an epoxide of the olefinic organic compound, aldehydes, carboxylic acids, and other organic products produced from the non-selective oxidation of the olefinic compound and also tertiary alcohol produced from the organic hydroperoxide.

In another embodiment of the invention, the olefinic compound is selected from the group consisting of styrene, substituted styrenes, cyclohexene, substituted cyclohexenes, 1-octene and other linear or non-linear normally gaseous and normally liquid olefins, norbornene, cyclopentene, cyclooctene, allylchloride, allyl alcohol and vinyl cyclohexene.

In another embodiment of the invention, the organic hydroperoxide is selected from the group consisting of tertiary butyl hydroperoxide, tertiary amyl hydroperoxide, cumene hydroperoxide, ethyl benzene hydroperoxide, cyclohexyl hydroperoxide and methyl cyclohexyl hydroperoxide.

In another embodiment of the invention, the catalyst is selected from the group consisting of potassium chromate, potassium dichromate, sodium chromate, sodium dichromate, ammonium chromate and ammonium dichromate.

In a further embodiment of the invention, the preferred organic hydroperoxide is selected from the group consisting of tertiary butyl hydroperoxide, cumene hydroperoxide and tertiary amyl hydroperoxide.

In yet another embodiment of the invention, the preferred mole ratio of organic hydroperoxide to olefinic compound is between 0.5 and 2.0.

In yet another embodiment of the invention, the preferred catalyst is potassium chromate or potassium dichromate.

In yet another embodiment of the invention, the preferred catalyst to olefinic compound weight ratio is between 0.001 and 0.1.

In yet another embodiment of the invention, the preferred temperature is between 50° C. and 150° C. and the preferred reaction period is between 1.0 h and 20 h.

In yet another embodiment of the invention, the preferred olefinic compound is selected from the group consisting of styrene, substituted styrene, cyclohexene, substituted cyclohexene, 1-octene and 1-hexene.

In yet another embodiment of the invention, the process is carried out in a stirred batch reactor fitted with a reflux condenser.

In another embodiment of the invention, the reflux condenser reflux condenser fitted with the reactor condenses the reactants, the products and/or water, and returns them back to the reaction mixture.

In the process of this invention, a reaction pressure above atmospheric pressure may be used to allow the reaction to be carried out at temperature higher than the normal boiling point of the reactants and/or solvent, by increasing the boiling point of said reactants and/or solvent with increasing the reaction pressure. In the first step of the process of this invention, liquid olefinic organic compound (I) reacts with organic hydroperoxide (II) to yield corresponding epoxide and other products in the presence of the catalyst (III). The role of the catalyst is to enhance rate of the epoxidation reaction and thereby to drastically reduce the time required for the reaction. The role of solvent water is to dissolve catalyst (III) and transfer it into the aqueous phase. The catalyst (III) of the process of this invention is present in an aqueous phase and hence can be removed or separated from the reaction mixture from the reaction mixture easily, simply by separating the aqueous phase containing the catalyst.

DETAILED DESCRIPTION OF THE INVENTION

The present invention provides a process for the epoxidation of olefinic compounds in a biphasic system using a novel catalyst comprising chromate or dichromate ions in aqueous solution. In the process of the invention, the main product is the epoxide of the olefinic organic compound used in the process and other products are aldehydes and carboxylic acids, and other organic products produced from the non-selective oxidation of the olefinic compound and also tertiary alcohol produced from the organic hydroperoxide.

A number of olefinic organic compounds are known in the prior art for example styrene, substituted styrenes, cyclohexene, substituted cyclohexenes, 1-octene and other linear or non-linear normally gaseous and normally liquid olefins, norbornene, cyclopentene, cyclooctene, allylchloride, allyl alcohol, vinyl cyclohexene and the like. The organic hydroperoxide is used as an oxidizing agent. Examples of organic hydroperoxides are tertiary butyl hydroperoxide, tertiary amyl hydroperoxide, cumene hydroperoxide, ethyl benzene hydroperoxide, cyclohexyl hydroperoxide, methyl cyclohexyl hydroperoxide and the like. The catalyst (III) is chromate or dichromate anions present in the aqueous medium. Examples of chromate or dichromate catalysts include potassium chromate or dichromate, sodium chromate or dichromate, ammonium chromate or dichromate and the like. The chromate or dichromate compounds are easily available and also quite inexpensive. They are also soluble in water and hence always used in aqueous phase in the process of this invention. The catalyst and the reactants and exist in two different phases, in the aqueous phase and non-aqueous (organic) phase, respectively:

In the process of the invention, the preferred organic hydroperoxide is tertiary butyl hydroperoxide or cumene hydroperoxide or tertiary amyl hydroperoxide; the preferred mole ration of organic hydroperoxide to olefinic compound is between 0.5 and 2.0; the preferred the catalyst is potassium chromate or potassium dichromate; the preferred catalyst to olefinic compound weight ratio is between 0.001 and 0.1; the preferred temperature is between 50° C. and 150° C.; the preferred reaction period is between 1.0 h and 20 h. and the preferred olefinic compound is styrene or substituted styrene or cyclohexene or substituted cyclohexene or 1-octene or 1-hexene.

The process of this invention can be carried out in a stirred batch reactor, fitted with a reflux condenser known in the prior art for carrying out liquid phase reactions. The role of the reflux condenser fitted with the reactor is to condense reactants, products and/or water, and to return them back to the reaction mixture. A reaction pressure above atmospheric pressure can be used to allow the reaction to be carried out at temperature higher than the normal boiling point of the reactants and/or solvent, by increasing the boiling point of said reactants and/or solvent with increasing the reaction pressure. Olefinic organic compound and organic hydroperoxide are reactants and are converted partly or completely to said products.

In the first step of the process of this invention, liquid olefinic organic compound reacts with organic hydroperoxide to yield corresponding epoxide and other products in the presence of the catalyst. The role of the catalyst is to enhance rate of the epoxidation reaction and thereby to drastically reduce the time required for the reaction. The role of solvent water is to dissolve catalyst and transfer it into the aqueous phase.

The catalyst of the process of this invention is present in an aqueous phase and hence can be removed or separated from the reaction mixture from the reaction mixture easily, simply by separating the aqueous phase containing the catalyst. After the reaction, the catalyst from the aqueous phase may be concentrated or removed and reused in the process of this invention. Products and unconverted reactants present in the non-aqueous phase may be separated by processes or methods such as distillation, extraction etc. known in the prior art.

The present invention is described with reference to the following examples illustrating the process of this invention for the liquid phase epoxidation illustrating the process of this invention for the liquid phase epoxidation of organic olefinic compound by organic hydroperoxide, using said catalyst comprising chromate or dichromate anions. However, these examples are provided for illustration purpose only and/or not to be construed as limitations on scope of the process of this invention.

Definitions of Terms used in the Examples

Conversion of reactant (%)=mole % of reactant converted in the process.

Selectivity of product (%)=[(mole % of reactant converted to the particular product)÷(mole % of reactant converted to all the products)]×100.

Abbreviation used: TBHP=tertiary butyl hydroperoxide; TAHP=tertiary amyl hydroperoxide; CHP=cumene hydroperoxide.

EXAMPLES 1–16

These examples illustrates the process of this invention for the liquid phase epoxidation of olefinic compounds by different organic hydroperoxides to corresponding epoxides using chromate or dichromate catalyst.

The process of this invention was carried out at atmospheric pressure by contacting the catalyst dissolved in water with a liquid reaction mixture containing a liquid olefinic compound and aqueous or non-aqueous organic hydroperoxide, (TAHP=Tertiary Amyl Hydroperoxide; CHP=cumene hydroperoxide) in a stirred batch reactor (capacity: 25 cm$^3$) and fitted with a reflux condenser and mercury thermometer dipped in the reaction mixture, under vigorous stirring at the reaction conditions given in Table-1, and after the reaction, cooling the reaction mixture close to room temperature separating using separating flask the aqueous layer containing the catalyst from the non-aqueous organic layer containing the reaction products and unconverted reactants and then analysing the products and unconverted reactants present in the non-aqueous reaction mixture by a gas chromatograph with a flame ionization detector, using a SE 30 column and nitrogen as a carrier gas.

Results of the epoxidation of olefinic compound by the process of this invention at different process conditions and using different olefinic compounds, organic hydroperoxides and catalysts of this invention are presented as Examples in Table-1. The results in Table-1 overleaf show that olefinic organic compounds can be converted into corresponding epoxides with high conversion and epoxide selectivity or yield.

TABLE 1

Results of the epoxidation of different olefinic compounds

| | Example No. | | | |
| --- | --- | --- | --- | --- |
| | Example-1 | Example-2 | Example-3 | Example-4 |
| Catalyst (III) | $K_2CrO_4$ | $K_2CrO_4$ | $K_2CrO_4$ | $K_2Cr_2O_7$ |
| Reactants | | | | |
| Olefinic compound (I) | Styrene | Cyclohexene | 1-Octene | 1-Hexene |
| Organic hydroperoxide (II) | Aq. TBHP (70 wt % TBHP in water) | Aq. TBHP (70 wt % TBHP in water) | Aq. TBHP (70 wt % TBHP in water) | Aq. TBHP (70 wt % TBHP in water) |
| Reaction conditions | | | | |
| II/I mole ratio | 1.0 | 1.0 | 1.0 | 1.0 |
| III/I weight ratio | 0.08 | 0.008 | 0.002 | 0.008 |
| Temperature (° C.) | 83 | 60 | 71 | 55 |
| Reaction in time (h) | 3.0 | 5.0 | 10 | 5.0 |
| Conversion of olefinic compound (I) (%) | 75.3 | 30.5 | 26.5 | 37.9 |
| Main product of the reaction | Styrene oxide | Cyclohexene oxide | Epoxy octane | Epoxy hexane |
| Selectivity for main product (%) | 69.3 | 86.3 | 63.1 | 59.7 |
| | Example No. | | | |
| | Example-5 | Example-6 | Example-7 | Example-8 |

TABLE 1-continued

Results of the epoxidation of different olefinic compounds

| Catalyst (III) | $K_2CrO_4$ | $K_2CrO_4$ | $K_2CrO_4$ | $K_2CrO_4$ |
|---|---|---|---|---|
| Reactants | | | | |
| Olefinic compound (I) | Styrene | Styrene | Styrene | Styrene |
| Organic hydroperoxide (II) | Aq. TBHP(70 wt % TBHP in water) | Aq. TBHP (70 wt % TBHP in water) | Aq. TBHP (70 wt % TBHP in water) | Aq. TBHP (70 wt % TBHP in water) |
| Reaction conditions | | | | |
| II/I mole ratio | 0.5 | 2.0 | 4.0 | 1.0 |
| III/I weight ratio | 0.008 | 0.008 | 0.009 | 0.008 |
| Temperature (° C.) | 80 | 82 | 81 | 50 |
| Reaction time (h) | 5.0 | 5.0 | 5.0 | 20.0 |
| Conversion of olefinic compound (I) (%) | 45.5 | 61.0 | 78.9 | 51.0 |
| Main products of the reaction | Styrene oxide and phenyl acetaldehyde | Styrene oxide and phenyl acetaldehyde | Styrene oxide and phenyl acetaldehyde | Styrene oxide and phenyl acetaldehyde |
| Selectivity for the main products (%) | 89.2 | 80.1 | 79.3 | 69.9 |

| | Example No. | | | |
|---|---|---|---|---|
| | Example-9 | Example-10 | Example-11 | Example-12 |
| Catalyst (III) | $K_2CrO_4$ | $K_2CrO_4$ | $K_2CrO_4$ | $K_2Cr_2O_7$ |
| Reactants | | | | |
| Olefinic compound (I) | Styrene | Styrene | Styrene | Styrene |
| Organic hydroperoxide (II) | Aq. TBHP (70 wt % TBHP in water) | Aq. TBHP (70 wt % TBHP in water) | Aq. TBHP (70 wt % TBHP in water) | Aq. TBHP (70 wt % TBHP in water) |
| Reaction conditions | | | | |
| II/I mole ratio | 1.0 | 1.0 | 1.0 | 1.0 |
| III/I weight ratio | 0.008 | 0.008 | 0.006 | 0.01 |
| Temperature (° C.) | 80 | 80 | 80 | 80 |
| Reaction time (h) | 1.0 | 2.0 | 1.0 | 2.0 |
| Conversion of olefinic compound (I) (%) | 30.3 | 46.9 | 35.6 | 60.3 |
| Main products of the reaction | Styrene oxide | Styrene oxide | Styrene oxide | Styrene oxide |
| Selectivity for the main products (%) | 46.9 | 61.3 | 65.3 | 67.1 |

| | Example No. | | | |
|---|---|---|---|---|
| | Example-13 | Example-14 | Example-15 | Example-16 |
| Catalyst (III) | $K_2CrO_4$ | $K_2CrO_4$ | $K_2CrO_4$ | $K_2CrO_4$ |
| Reactants | | | | |
| Olefinic compound (I) | Styrene | Styrene | Styrene | Styrene |
| Organic hydroperoxide (II) | Cumene hydroperoxide | Tertiary amyl hydroperoxide | Tertiary amyl hydroperoxide | Cumene hydroperoxide |
| Reaction conditions | | | | |
| II/I mole ratio | 1.2 | 1.1 | 1.5 | 1.0 |
| III/I weight ratio | 0.01 | 0.008 | 0.008 | 0.007 |
| I/water wt. ratio | 1.5 | 1.0 | 2.0 | 5.0 |
| Temperature (° C.) | 100 | 80 | 95 | 97 |
| Reaction time (h) | 5.0 | 5.0 | 5.0 | 5.0 |
| Conversion of olefinic compound (I) (%) | 69.1 | 63.5 | 71.3 | 61.2 |
| Main products of the reaction | Styrene oxide | Styrene oxide | Styrene oxide | Styrene oxide |
| Selectivity for the main products (%) | 61.5 | 63.1 | 69.4 | 61.3 |

The main finding of this invention is that the catalyst of this invention, chromate or dichromate in aqueous medium, has high activity and epoxide selectivity in the process of this invention. Because of the high activity of the catalyst of this invention, time required for obtaining conversion of the olefinic compound (I) of practical interest, about 20%, is short.

The catalyst of this invention can be easily removed from the reaction mixture, simply by separating the aqueous layer which contains the catalyst, from the non-aqueous layer, which contains the organic compounds—epoxide, unreacted olefinic compound, organic hydroperoxide and other organic products.

Advantages of the Invention:
i) The process of this invention uses a novel catalyst comprising chromate or dichromate anions present in an aqueous phase and this catalyst shows both high activity and epoxide selectivity in the liquid phase epoxidation of olefinic compounds.
ii) In the process of this invention, the catalyst and the reactant exists in two different liquid phases-in the aqueous phase and in the organic phase, respectively.
iii) The catalyst of the process of this invention can be separated from the organic reaction mixture easily, simply by phase separation i.e. by removing the aqueous phase, which contains the catalyst.
iv) The catalyst of the process of this invention may be reused after recovering it from the aqueous phase after the reaction.

We claim:

1. A biphasic process for the liquid phase epoxidation of an olefinic compound comprising at least one olefinic group to an epoxide by an organic hydroperoxide, using a catalyst comprising chromate or dichromate anions, the process comprising:
   (i) contacting a liquid mixture containing the olefinic compound and the organic hydroperoxide compound with an aqueous solution of the catalyst in a stirred batch reactor in the presence of water such that the olefinic compound and the organic hydroperoxide are present in non-aqueous organic phase and the catalyst is present in dissolved form in aqueous phase; the mole ratio of organic hydroperoxide to olefinic compound being in the range of 0.1 to 10, the weight ratio of catalyst to olefinic compound being in the range of 0.0005 to 0.5;
   (ii) separating the aqueous layer containing the catalyst; and
   (iii) separating the reaction products and unconverted reactants from the non-aqueous organic phase.

2. A process as claimed in claim 1 wherein the contacting in step (i) is carried out at a temperature in the range of 25° to 250° and for a contacting period in the range of 0.1 h to 100 h and at a pressure of at least 1 atm.

3. A process as claimed in claim 1 wherein the reaction products comprise an epoxide of the olefinic organic compound, aldehydes, carboxylic acids, and organic products produced from the non-selective oxidation of the olefinic compound and also tertiary alcohol produced from the organic hydroperoxide.

4. A process as claimed in claim 1 wherein the olefinic compound is selected from the group consisting of styrene, substituted styrenes, cyclohexene, substituted cyclohexenes, 1-octene and normally gaseous and normally liquid olefins, norbornene, cyclopentene, cyclooctene, allylchloride, allyl alcohol and vinyl cyclohexene.

5. A process as claimed in claim 1 wherein the organic hydroperoxide is selected from the group consisting of tertiary butyl hydroperoxide, tertiary amyl hydroperoxide, cumene hydroperoxide, ethyl benzene hydroperoxide, cyclohexyl hydroperoxide and methyl cyclohexyl hydroperoxide.

6. A process as claimed in claim 1 wherein the catalyst is selected from the group consisting of potassium chromate, potassium dichromate, sodium chromate, sodium dichromate, ammonium chromate and ammonium dichromate.

7. A process as claimed in claim 1 wherein the organic hydroperoxide is selected from the group consisting of tertiary butyl hydroperoxide, cumene hydroperoxide and tertiary amyl hydroperoxide.

8. A process as claimed in claim 1 wherein step (i) is carried out at a mole ratio of organic hydroperoxide to olefinic compound of between 0.5 and 2.0.

9. A process as claimed in claim 1 wherein the catalyst is selected from the group consisting of potassium chromate and potassium dichromate.

10. A process as claimed in claim 1 wherein the catalyst to olefinic compound weight ratio during step (i) is between 0.001 and 0.1.

11. A process as claimed in claim 1 wherein step (i) temperature is between 50° C. and 150° and the reaction period is between 1.0 h and 20 h.

12. A process as claimed in claim 1 wherein the olefinic compound is selected from the group consisting of styrene, substituted styrene, cyclohexene, substituted cyclohexene, 1-octene and 1-hexene.

13. A process as claimed in claim 1 wherein the process is carried out in a stirred batch reactor fitted with a reflux condenser to condense the reactants, products and/or water and recycle them back to the process.

14. A process as claimed in claim 1 wherein a reaction pressure above atmospheric pressure is used to enable carrying out the contacting at a temperature higher than the normal boiling point of the reactants and/or solvent, by increasing the boiling point of said reactants and/or solvent with increasing the reaction pressure.

15. A process as claimed in claim 1 wherein the catalyst separated from the reactor and recycled back to the reaction mixture.

* * * * *